United States Patent
Atzler et al.

(10) Patent No.: US 10,082,466 B2
(45) Date of Patent: Sep. 25, 2018

(54) METHODS AND SYSTEMS FOR OPTICAL-BASED MEASUREMENT WITH SELECTABLE EXCITATION LIGHT PATHS

(71) Applicant: Molecular Devices, LLC, Sunnyvale, CA (US)

(72) Inventors: Josef J. Atzler, Hallein (AT); Michael Katzlinger, Eugendorf (AT); Klaus Wagner, Henndorf a.W. (AT)

(73) Assignee: Molecular Devices, LLC, San Jose, CA (US)

(*) Notice: Subject to any disclaimer, the term of this patent is extended or adjusted under 35 U.S.C. 154(b) by 196 days.

(21) Appl. No.: 15/138,660

(22) Filed: Apr. 26, 2016

(65) Prior Publication Data

US 2017/0307528 A1    Oct. 26, 2017

(51) Int. Cl.
    *G01N 21/64*    (2006.01)
(52) U.S. Cl.
    CPC ... *G01N 21/6428* (2013.01); *G01N 2201/061* (2013.01); *G01N 2201/063* (2013.01)
(58) Field of Classification Search
    CPC ......... G01N 21/6428; G01N 2201/063; G01N 2201/061
    USPC ............................................ 250/459.1, 458.1
    See application file for complete search history.

(56) References Cited

U.S. PATENT DOCUMENTS

| | | | |
|---|---|---|---|
| 4,455,097 A | 6/1984 | Ichikawa et al. | |
| 8,119,066 B2 | 2/2012 | Stock et al. | |
| 8,218,141 B2 | 7/2012 | Zimenkov et al. | |
| 9,134,243 B2 | 9/2015 | Wilson et al. | |
| 9,188,527 B2 | 11/2015 | Atzler et al. | |
| 2005/0122521 A1 | 6/2005 | Katzlinger et al. | |
| 2008/0191149 A1* | 8/2008 | Zimenkov | G01J 3/10 250/492.1 |
| 2012/0300194 A1 | 11/2012 | Zimenkov et al. | |
| 2013/0119277 A1 | 5/2013 | Atzler et al. | |
| 2014/0191138 A1 | 7/2014 | Atzler et al. | |

OTHER PUBLICATIONS

International Search Report and Written Opinion for PCT/US2017/029550 dated Jul. 18, 2017.

* cited by examiner

*Primary Examiner* — David Porta
*Assistant Examiner* — Gisselle Gutierrez (57) ABSTRACT

In an optical-based sample analysis, for example fluorescence-based or absorbance-based measurement, a selection is made between a first excitation light path and a second excitation light path. The first excitation light path directs excitation light from a light source, through an excitation monochromator, through an excitation filter, and to a sample. The second excitation light path directs excitation light from the light source, through the excitation filter, and to the sample while bypassing the excitation monochromator. Excitation light generated by the light source is transmitted along either the first excitation light path or the second excitation light path in accordance with the selection made, thereby irradiating the sample. In response the sample produces emission light (transmitted light in the case of absorbance measurements), which is transmitted to and measured by a light detector.

20 Claims, 6 Drawing Sheets

METHODS AND SYSTEMS FOR OPTICAL-BASED MEASUREMENT WITH SELECTABLE EXCITATION LIGHT PATHS

TECHNICAL FIELD

The present invention generally relates to methods, apparatuses, and systems for optical-based measurement of samples, such as fluorescence-based or absorbance-based measurement. In particular, the invention relates to implementing wavelength selection of excitation light by selecting among different excitation light paths, one of which includes a monochromator and another of which bypasses the monochromator.

BACKGROUND

Various analytical instruments have been developed for making optics-based measurements (e.g., fluorescence, luminescence, and absorbance) on samples (e.g., chemical compounds, biological material, etc.) as part of assays useful in the life science industry. Many analytical instruments are designed to carry out only one or a few dedicated types of measurements. On the other hand, multimode analytical instruments, also referred to as multimode readers, are designed to perform multiple analytical assays in a single instrument. Multimode analytical instruments may be designed to be re-configurable to enable a user to select different types of measurements to be performed. Some multimode analytical instruments utilize application-specific cartridges to enable re-configuration.

Some types of measurements, such as fluorescence and absorbance measurements, require that the sample be irradiated with a beam of light, referred to herein as "excitation" light. In the case of fluorescence measurements, the excitation light is needed to induce fluorescence in the sample. In a typical example, the sample is irradiated with excitation light of a relatively short wavelength, and in response emits fluorescent light of a relatively longer wavelength. This "emission" light is measured by a suitable light detector, which often is a photomultiplier tube (PMT) in the case of fluorescence measurements. In the case of absorbance measurements, the excitation light is needed when the absorbance measurement is based on comparing the amount of the excitation light transmitted through the sample versus the amount of the excitation light incident on the sample. Measurements requiring excitation light may further require that the excitation light utilized to irradiate the sample be limited to a specific wavelength or very narrow band of wavelengths. In the case of fluorescence measurements, the fluorescent response may require a specific excitation wavelength. In the case of absorbance measurements, the light detector utilized (often a photodiode in the case of absorbance measurements) may have an optimum sensitivity at a certain wavelength or very narrow band of wavelengths.

Thus, wavelength-selection devices have been utilized in the excitation light path (as well as the emission light path) of optical-based analytical instruments. Wavelength-selection devices include monochromators and optical filters, the design and operation of which are familiar to persons skilled in the art. It is also known that advantages and disadvantages are associated with both monochromators and optical filters. Depending on the type of measurement to be performed, the type of sample under analysis, and other factors, one type of wavelength-selection device may be preferred over others. In some situations, it would be useful to employ two different types of wavelength-selection devices (e.g., a monochromator and an optical filter) in tandem, while in other situations it would be useful to employ one type of wavelength-selection device while bypassing the other type of wavelength-selection device.

SUMMARY

To address the foregoing problems, in whole or in part, and/or other problems that may have been observed by persons skilled in the art, the present disclosure provides methods, processes, systems, apparatus, instruments, and/or devices, as described by way of example in implementations set forth below.

According to an embodiment, a method for analyzing a sample by optical-based measurement includes: selecting between a first excitation light path and a second excitation light path, wherein: the first excitation light path directs excitation light from a light source, through an excitation monochromator, through an excitation filter, and to the sample; and the second excitation light path directs excitation light from the light source, through the excitation filter, and to the sample while bypassing the excitation monochromator; generating excitation light at the light source; irradiating the sample by transmitting the generated excitation light along the selected one of the first excitation light path and the second excitation light path, wherein irradiating the sample produces emission light; and measuring the emission light by transmitting the emission light to a light detector.

According to another embodiment, a sample analyzing apparatus or system is configured for performing all or part of any of the methods disclosed herein.

According to another embodiment, a sample analyzing apparatus or system for performing an optical-based measurement on a sample, includes: a light source configured for generating excitation light; a light detector configured for measuring the emission light; and an excitation light path selection device configured for selecting between the first excitation light path and the second excitation light path in accordance with any of the methods disclosed herein.

According to another embodiment, a sample analyzing apparatus or system for performing an optical-based measurement on a sample, includes: a light source configured for generating excitation light; excitation optics configured for directing the excitation light from the light source to the sample, wherein the sample produces emission light in response to being irradiated by the excitation light; a light detector configured for measuring the emission light; and emission optics configured for directing the emission light from the sample to the light detector, wherein: the excitation optics comprise an excitation filter, an excitation monochromator, and an excitation light path selection device configured for selecting between a first excitation light path and a second excitation light path; the first excitation light path directs excitation light from a light source, through an excitation monochromator, through an excitation filter, and to the sample; and the second excitation light path directs excitation light from the light source, through the excitation filter, and to the sample while bypassing the excitation monochromator.

Other devices, apparatuses, systems, methods, features and advantages of the invention will be or will become apparent to one with skill in the art upon examination of the following figures and detailed description. It is intended that all such additional systems, methods, features and advantages be included within this description, be within the scope of the invention, and be protected by the accompanying claims.

BRIEF DESCRIPTION OF THE DRAWINGS

The invention can be better understood by referring to the following figures. The components in the figures are not necessarily to scale, emphasis instead being placed upon illustrating the principles of the invention. In the figures, like reference numerals designate corresponding parts throughout the different views.

DETAILED DESCRIPTION

As used herein, the term "analyte" generally refers to a substance to be detected or measured by an optical-based technique. Examples of analytes include, but are not limited to, proteins (including membrane-bound proteins), antigenic substances, haptens, antibodies, toxins, organic compounds, peptides, microorganisms, amino acids, nucleic acids, hormones, steroids, vitamins, drugs (including those administered for therapeutic purposes as well as those administered for illicit purposes), drug intermediaries or byproducts, bacteria, virus particles and metabolites of or antibodies to any of the foregoing (as applicable), and combinations of two or more of any of the foregoing.

As used herein, the term "sample" generally refers to a material known or suspected of containing the analyte. In implementing the subject matter disclosed herein, the sample may be utilized directly as obtained from the source or following a pretreatment to modify the character of the sample. The sample may be derived from any biological source, such as a physiological fluid, including for example blood, interstitial fluid, saliva, ocular lens fluid, cerebral spinal fluid, sweat, urine, milk, ascites fluid, raucous, synovial fluid, peritoneal fluid, vaginal fluid, amniotic fluid or the like. The sample may be pretreated prior to use, such as preparing plasma from blood, diluting viscous fluids, and the like. Methods of pretreatment can involve filtration, precipitation, dilution, distillation, concentration, inactivation of interfering components, chromatography, separation steps, and the addition of reagents. Besides physiological fluids, other liquid samples may be used such as water, food products and the like for the performance of environmental or food production assays. In addition, a solid material known or suspected of containing the analyte may be used as the sample. In some instances it may be beneficial to modify a solid sample to form a liquid medium or to release the analyte from the solid sample.

As used herein, the term "light" generally refers to electromagnetic radiation, quantizable as photons. As it pertains to the present disclosure, light may propagate at wavelengths ranging from ultraviolet (UV) to infrared (IR). In the present disclosure, the term "light" is not intended to be limited to electromagnetic radiation in the visible range. In the present disclosure, the terms "light," "photons," and "radiation" are used interchangeably.

As used herein, in relation to the detection or measurement of optical signals emanating from a sample, terms such as "emission light" or "emitted light" refer to light emitted from the sample as a consequence of fluorescence or luminescence. Additionally, for convenience terms such as "emission light" or "emitted light" also refer to light that is transmitted through a sample and collected for the purpose of measuring absorbance.

Figure 1:
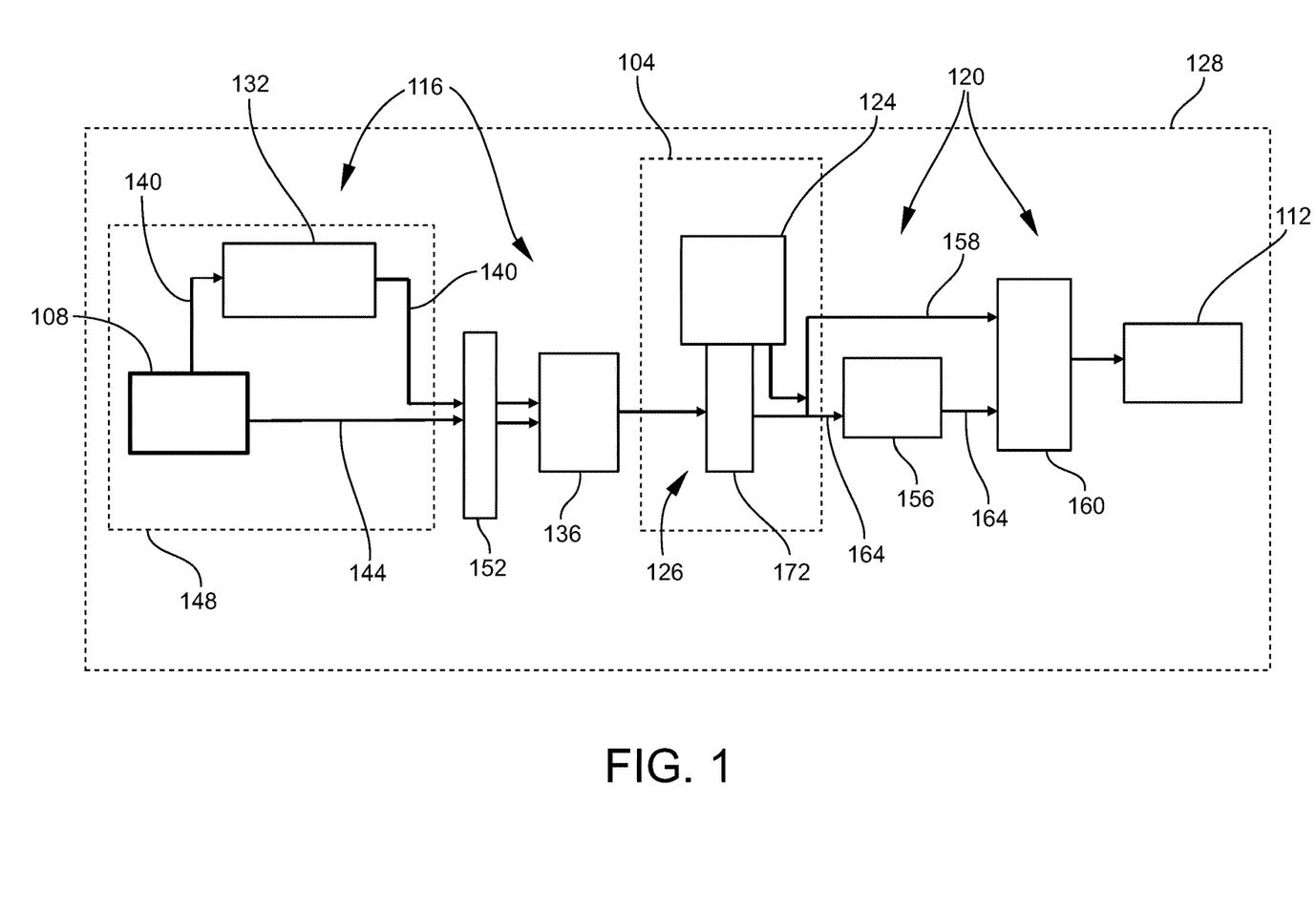
FIG. 1 is a schematic view of an example of a sample analyzing apparatus according to an embodiment disclosed herein.
Figure 2:
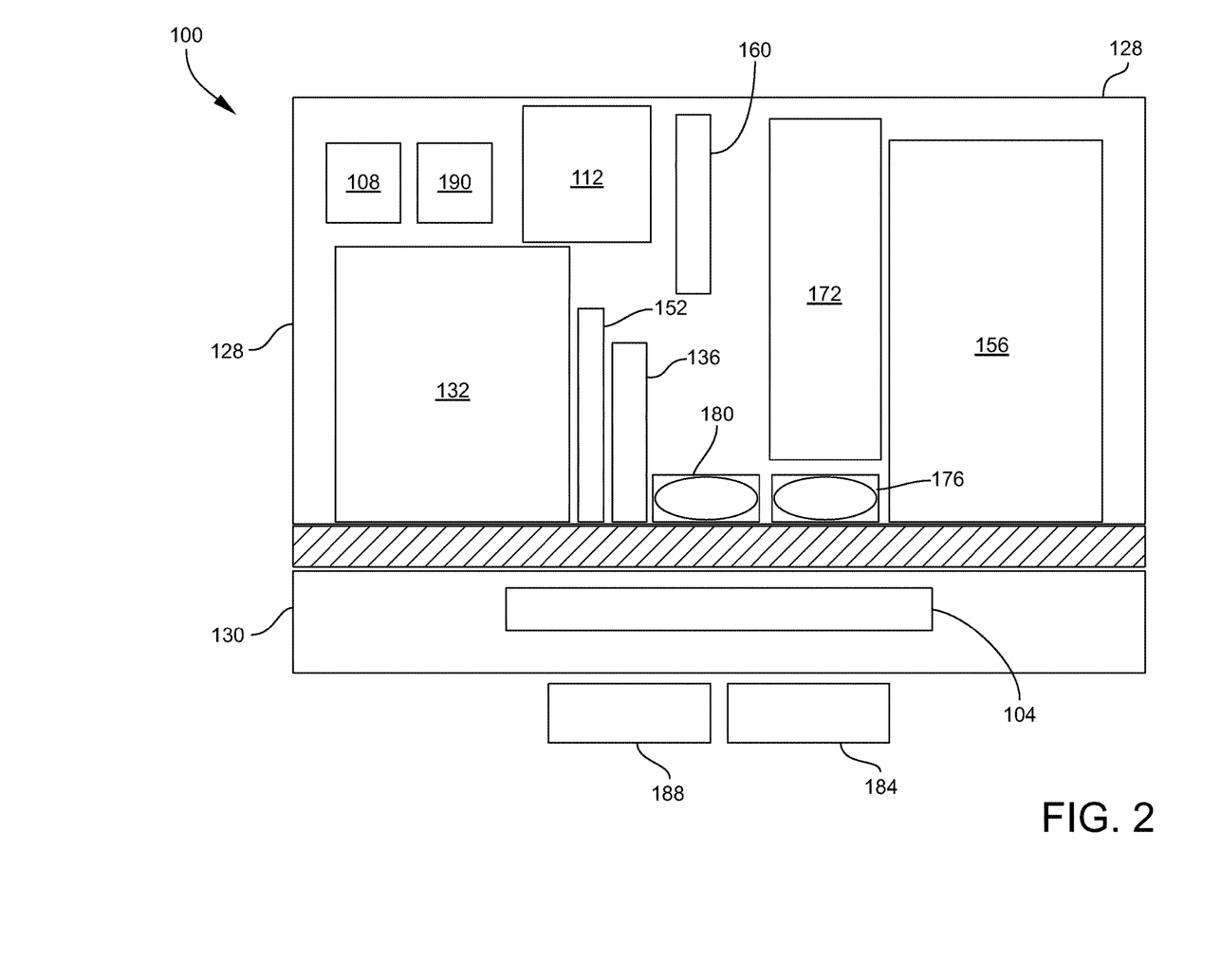
FIG. 2 is another schematic view of the sample analyzing apparatus.

FIG. 1 is a schematic view of an example of a sample analyzing apparatus 100 according to some embodiments. In FIG. 1, the various components of the sample analyzing apparatus 100 are schematically arranged generally in the overall direction of light transmission from one component to another component. FIG. 2 is another schematic view of the sample analyzing apparatus 100. FIG. 2 may generally be taken to be an elevation view, with the understanding that the components generally have been arranged in an arbitrary manner. In actual embodiments, the relative positions of the components to each other may differ significantly from what is schematically depicted or suggested in FIGS. 1 and 2.

The sample analyzing apparatus 100 is configured for performing one or more types of optical-based measurements on a sample (or on multiple samples) to detect or measure analytes of interest. In some embodiments, the sample analyzing apparatus 100 is configured to enable a user to select a desired type of optical measurement to be performed, such as measurements based on fluorescence, absorbance, luminescence, cell imaging, etc. For example, the user may be able to reconfigure the optics of the sample analyzing apparatus 100 to perform a desired type of optical measurement. Thus, in some embodiments the sample analyzing apparatus 100 may be a multi-mode reader. For example, as a multi-mode reader the sample analyzing apparatus 100 may be reconfigurable by enabling a user to select an application-specific cartridge among a number of different cartridges available, and load the selected cartridge into the sample analyzing apparatus 100 so as to establish optical and electrical circuits specific to the desired application. In this manner, the selected cartridge may be operatively coupled to the sample analyzing apparatus 100 whereby the sample analyzing apparatus 100 is properly configured for carrying out the selected experiment. Each cartridge may contain internal optics specific to or optimized for a particular type of experiment (e.g., fluorescence, absorbance, luminescence, etc.). The internal optics housed within the cartridge may communicate with external optics housed within the housing of the sample analyzing apparatus 100 through optical ports of the cartridge's housing. Some cartridges may additionally include one or more internal light sources and/or one or more internal light detectors. The sample analyzing apparatus 100 may be configured to receive and support more than one cartridge at the same time, and a particular cartridge may thereafter be selected for coupling into the optical path defined by the sample analyzing apparatus 100, such as by moving the selected cartridge to an operative position in the interior of the sample analyzing apparatus 100. Examples of cartridge-based multi-mode readers are described in U.S. Pat. Nos. 9,188,527 and 8,119,066, the contents of which are incorporated by reference herein in their entireties.

Generally, the structure and operation of the various components provided in optical-based sample analysis instruments are understood by persons skilled in the art, and thus are only briefly described herein to facilitate an understanding of the presently disclosed subject matter. In the illustrated embodiment, the sample analyzing apparatus 100 includes a sample carrier 104 configured for supporting one or more samples under analysis, a light source 108 for generating excitation light, a light detector 112 for receiving and measuring emission light propagating from the sample (e.g., by fluorescence or luminescence), excitation optics 116 configured for directing the excitation light along an excitation light path from the light source 108 to the sample and processing or modifying the excitation light in one or more ways, and emission optics 120 configured for directing emission light along an emission light path from the sample (e.g., emitted by the sample by fluorescence or luminescence) to the light detector 112 and processing or modifying the excitation light in one or more ways. When configured as a multi-mode reader, the sample analyzing apparatus 100 may further include a cartridge module 124 configured to removably receive and support and plurality of application-specific cartridges configured for implementing specific optics-based measurements (e.g., fluorescence, absorbance, luminescence, etc.) as described above, and intermediate or interface optics 126 configured for providing optical interfaces between a selected cartridge and the excitation optics 116 and emission optics 120. The sample analyzing apparatus 100 further includes an apparatus housing 128 that encloses the sample carrier 104 and cartridge module 124 (when in operative positions for carrying out optical measurements on the sample), as well as other components of the sample analyzing apparatus 100 such as the light source 108, light detector 112, excitation optics 116, and emission optics 120. The apparatus housing 128 may include one or more panels, doors, drawers, etc. for allowing access to interior regions of the sample analyzing apparatus 100, including for loading samples onto the sample carrier 104 and cartridges into the cartridge module 124. The sample analyzing apparatus 100 may further include an incubation chamber 130 (FIG. 2) in the apparatus housing 128, at which the sample(s) (supported on the sample carrier 104) may be operatively located.

Generally, the sample carrier 104 is configured for moving one or more samples along one or more axes. For example, the sample carrier 104 may be an X-Y stage movable in two dimensions in a horizontal plane, although in other embodiments may also be movable in a third vertical (Z) dimension. The sample carrier 104 may be a manually actuated, semi-automated, or fully-automated (motorized) stage or platform. In typical embodiments, one or more samples are supported or held by a suitable sample support, which is in turn supported by the sample carrier 104. Generally, the sample support may be one or more containers configured for holding one or more samples during an analysis. As non-limiting examples, the sample support may be a multi-well plate (also known as a microtiter plate, microplate, or optical plate), one or more cuvettes or vials, a substrate supporting spots or blots containing respective samples, etc. The sample carrier 104 may be movable into and out from the apparatus housing 128. Thus a sample, or sample support that supports one or more samples, may be mounted onto the sample carrier 104 while the sample carrier 104 is at an outside position, e.g., where the sample carrier 104 is positioned at least partially outside the apparatus housing 128. The sample carrier 104 may then be moved to an inside position at which the sample carrier 104 is positioned entirely in the apparatus housing 128 (as illustrated in FIG. 1) so as to align the sample (or successively align multiple samples) with one or more optical components of the sample analyzing apparatus 100.

The light source 108 is utilized in embodiments requiring excitation (irradiation) of the sample, such as fluorescence and absorbance detection techniques. In some embodiments, the light source 108 is a broadband light source such as a flash lamp (e.g., a xenon flash lamp, deuterium flash lamp, halogen flash lamp, metal halide flash lamp, etc.), which may be configured to produce a pulsed light beam. In other embodiments, other light sources such as light emitting diodes (LEDs), laser diodes (LDs), lasers, etc. may be provided, and the sample analyzing apparatus 100 may be configured to enable switching between different types of light sources, as appreciated by persons skilled in the art.

Generally, the excitation optics 116 may include, for example, one or more lenses, apertures, filters, light guides (e.g., optical fibers), mirrors, beam splitters, monochromators, diffraction gratings, prisms, optical path switches, etc. In the present embodiment, the excitation optics 116 include an excitation monochromator 132 and an excitation filter holder 136. As appreciated by persons skilled in the art, the excitation monochromator 132 and the excitation filter holder 136 both function as wavelength selectors for controlling the specific wavelength (or narrow band of wavelengths) of the excitation light to be passed further through the optical system. That is, the excitation monochromator 132 and the excitation filter holder 136 both function to receive the excitation light from the light source 108 and transmit the excitation light onwards at a desired wavelength or narrow band of wavelengths (colors), but operate on different principles.

The excitation monochromator 132 comprises one or more diffraction gratings that spatially separate the different wavelengths of the excitation light. The excitation monochromator 132 transmits the component of the excitation light having a selected wavelength by rotating the diffraction grating(s) to a position that aligns the excitation light having the selected wavelength with an exit slit. All components of the excitation light having non-selected wavelengths are not aligned with the exit slit, and thus are blocked from propagating in the optical path beyond the excitation monochromator 132.

On the other hand, the excitation filter holder 136 supports a plurality of optical filters composed of materials having different optical transmission characteristics. That is, the optical filters are formulated to pass different wavelengths of the excitation light. The excitation filter holder 136 is configured so as to be movable, either by rotation or (in the illustrated embodiment) linear translation (i.e., sliding). Hence, the excitation filter holder 136 may be actuated so as to move a selected filter into the optical path, whereby the selected filter allows passage of only the selected wavelength (or narrow band of wavelengths) onward in the optical path beyond the excitation filter holder 136, while blocking all other wavelengths. In one embodiment the excitation filter holder 136 comprises eight positions, including up to six positions occupied by optical filters (e.g., long pass, short pass, band pass, etc.), another position being an open aperture through which the excitation light can pass without any interference, and another position presenting a material that blocks the excitation light completely.

In some embodiments the excitation filter holder 136 may include a main near-field communications (NFC) tag utilized to store information regarding all of the filters positioned at the excitation filter holder 136. The excitation filter holder 136 may also include individual NFC tags for each filter (e.g., located at each filter position). The sample analyzing apparatus 100 may include an NFC antenna positioned such that when the excitation filter holder 136 is loaded into the sample analyzing apparatus 100, the NFC antenna reads the information associated with any filter positioned in front of the NFC antenna. When the main NFC tag is positioned in front of the NFC antenna the specific information associated with the filter may be stored on the main NFC tag.

In the present embodiment, the optical path provided for excitation light to be transmitted from the light source 108 to the excitation filter holder 136 is split into a first excitation light path 140 and a second excitation light path 144. As schematically illustrated in FIG. 1, the excitation monochromator 132 is in (i.e., optically communicates with, or operates in) the first excitation light path 140 only. Thus, the first excitation light path 140 directs excitation light from the light source 108, through the excitation monochromator 132, through the selected excitation filter of the excitation filter holder 136, and onward to the sample (appropriately positioned at the sample carrier 104). The second excitation light path 144 directs excitation light from the light source 108, through the selected excitation filter of the excitation filter holder 136, and to the sample while bypassing the excitation monochromator 132. The sample analyzing apparatus 100 is configured for switching the optical path between the first excitation light path 140 and the second excitation light path 144. In other words, the sample analyzing apparatus 100 is configured for selecting whether the excitation light generated by the light source 108 is directed through the first excitation light path 140 or through the second excitation light path 144, and thereby selects whether or not the excitation monochromator 132 is bypassed. For this purpose, the excitation optics 116 include an excitation path selection device 148. As described further below, the excitation path selection device 148 is movable (can be actuated to move) so as to direct the excitation light from the light source 108 into either the first excitation light path 140 or the second excitation light path 144. As will also become evident, the excitation path selection device 148 may comprise only a single movable component, i.e., only a single movable component is needed to guide the excitation light into the selected (first or second) excitation light path 140 or 144.

As also illustrated in FIG. 1, in some embodiments the excitation optics 116 may further include an additional optics holder 152 that holds a plurality of different optics components. The additional optics holder 152 is movable (by rotation or sliding) so as to insert a selected optics component into the first excitation light path 140 between the excitation monochromator 132 and the excitation filter holder 136, and into the second excitation light path 144 between the light source 108 and the excitation filter holder 136. The additional optics holder 152 may include one or more attenuation filters providing different attenuation factors (e.g., no attenuation, 10D, 20D, 30D, etc.) to reduce the energy of the excitation light in the event that samples with a high response are measured that would saturate the light detector 112. A reference beam splitter (not shown) following the additional optics holder 152 may split off a portion of the excitation light beam as a reference beam that is directed to a reference photodiode (note shown). The reference photodiode may be utilized to track the energy of the excitation light. Based on the intensity of the excitation light measured by the reference photodiode, a system controller (computing device) 190 (FIG. 2) of the sample analyzing apparatus 100 may attenuate the excitation light by actuating the additional optics holder 152 to move so as to insert an attenuation filter of a selected attenuation factor into the active excitation light path 140 or 144. Such technique of dynamic range extension may be implemented as described in U.S. Patent Application Publication No. 2013/0119277, the entire contents of which are incorporated by reference herein. In addition or as an alternative to attenuation filters, other examples of optics components that may be positioned at the additional optics holder 152 include, but are not limited to, beam-shaping apertures, open apertures (i.e., apertures that do not attenuate or modify the light beam passing therethrough), and filters with specialized functions (e.g., long pass, short pass, band pass, etc.).

Generally, the emission optics 120 may include, for example, one or more lenses, apertures, filters, light guides (e.g., optical fibers), mirrors, beam splitters, monochromators, diffraction gratings, prisms, optical path switches, etc. In the present embodiment, the emission optics 120 include an emission monochromator 156 and an emission filter holder 160. The emission filter holder 160 may support a plurality of emission filters having different light transmission characteristics. The emission monochromator 156 and the emission filter holder 160 may generally be similar to the excitation monochromator 132 and the excitation filter holder 136 described herein, and may be optimized as needed for use in the emission light path.

In the present embodiment, the optical path provided for emission light to be transmitted from the sample (or intervening cartridge and/or interface optics 126, depending on the measurement technique being implemented) to the light detector 112 is split into a first emission light path 164 and a second emission light path 168. As schematically illustrated in FIG. 1, the emission monochromator 156 is in (i.e., optically communicates with, or operates in) the first emission light path 164 only. Thus, the first emission light path 164 directs emission light through the emission monochromator 156, through the selected emission filter of the emission filter holder 160, and onward to the light detector 112. The second emission light path 168 directs emission light through the selected emission filter of the emission filter holder 160, and to the light detector 112 while bypassing the emission monochromator 156. The sample analyzing apparatus 100 is configured for switching the emission light path between the first emission light path 164 and the second emission light path 168. In other words, the sample analyzing apparatus 100 is configured for selecting whether or not the emission monochromator 156 is bypassed. In the present embodiment, the interface optics 126 include a main optical path selection device 172 configured for switching between the first emission light path 164 and the second emission light path 168.

Generally, the light detector 112 is configured to generate electrical measurement signals in response to receiving emission light signals from the emission optics 120, and transmit the measurement signals to signal processing circuitry (e.g., data acquisition circuitry) provided with or external to the sample analyzing apparatus 100 (e.g., as generally represented by the system controller 190). Depending on the embodiment, the light detector 112 may be a photomultiplier tube (PMT), a photodiode, a chargecoupled device (CCD), an active-pixel sensor (APS) such as a complementary metal-oxide-semiconductor (CMOS) device, etc., as needed to optimize sensitivity to the emission wavelengths to be detected. In a typical embodiment, the illustrated light detector 112 comprises one or more PMTs optimized for processing fluorescence and/or luminescence emission light signals. A separate light detector (not shown in FIGS. 1 and 2) optimized for processing absorbance emission light signals, such as a photodiode, may be provided.

As described above, the cartridge module 124 is configured to removably receive and support and plurality of application-specific cartridges configured for implementing specific optics-based measurements (e.g., fluorescence, absorbance, luminescence, etc.). For this purpose, the cartridge module 124 may include a plurality of receptacles or slots into which individual cartridges may be installed (loaded) and thereafter uninstalled (removed). The cartridge module 124 may be movable in an automated, semi-automated, or manual manner. For example, the cartridge module 124 may be movable through a door of the apparatus housing 128 to an at least partially outside position that facilitates installation and uninstallation of cartridges. As another example, the cartridge module 124 may be movable within the interior of the apparatus housing 128 to enable a selected cartridge to be optically aligned with the optical system of the sample analyzing apparatus 100 (i.e., placed in optical communication with the excitation optics 116 and emission optics 120). Depending on the type of experiment for which a given cartridge is utilized, the internal optics enclosed by the cartridge housing of the cartridge may include various components such as, for example, mirrors, filters, prisms, diffraction gratings, internal light sources, and/or internal light detectors.

Generally, the interface optics 126 may include, for example, one or more lenses, optical read heads, apertures, filters, light guides (e.g., optical fibers), mirrors, beam splitters, optical path switches, etc. In the present embodiment, the interface optics 126 include the main optical path selection device 172. In addition to being configured to switch between the first emission light path 164 and the second emission light path 168, the main optical path selection device 172 may be configured to select a measurement method by selecting appropriate optical paths between the excitation optics 116 and the sample, and between the sample and the emission optics 120. The main optical path selection device 172 may also be configured to select whether the cartridge module 124 (i.e., a specific cartridge installed in the cartridge module 124) is placed in optical communication with (is inserted into) the optical path (excitation light path and/or emission light path). For these purposes, the main optical path selection device 172 may include a structural body at which various optical components are mounted, attached, or formed, such as, for example, one or more lenses, apertures, light guides (e.g., optical fibers), mirrors, beam splitters, etc. The structural body of the main optical path selection device 172 may provide a plurality of selectable positions, and may be movable (e.g., slidable) to select which position is to be the operable or active position in the optical path.

As illustrated in FIG. 2, the interface optics 126 may further include a top absorbance lens 176 (a lens utilized for absorbance measurements) positioned above the sample carrier 104 (in alignment with a selected sample supported on the sample carrier 104), a top fluorescence/luminescence lens 180 (a lens utilized for fluorescence and luminescence measurements) positioned above the sample carrier 104 (in alignment with a selected sample supported on the sample carrier 104), a bottom absorbance read head 184 positioned below the sample carrier 104 (in alignment with a selected sample supported on the sample carrier 104), and a bottom fluorescence read head 188 positioned below the sample carrier 104 (in alignment with a selected sample supported on the sample carrier 104). In some embodiments, the top fluorescence/luminescence lens 180 may be movable toward and away from the sample to accommodate different multi-well plate sizes, fill volumes, sample heights, etc., and to avoid cross-talk among neighboring wells of the multi-well plate.

The selection of a measurement method may entail operating the excitation path selection device 148 to select the first excitation light path 140 or the second excitation light path 144 as described herein, in conjunction with operating the main optical path selection device 172 to select a position. As one non-limiting example, the main optical path selection device 172 may provide the following selectable positions.

Position 0: This position may be utilized to couple an application-specific cartridge of the cartridge module 124 into the optical path to provide extended system capabilities, such as time-resolved fluorescence, multiplexed time-resolved fluorescence, fluorescence polarization, ALPHASCREEN® assays, NANO-TRF® assays, etc.

Position 1: This position may be utilized for absorbance measurements in conjunction with the excitation monochromator 132 and the excitation filter holder 136. The excitation light beam is directed to the top absorbance lens 176. The top absorbance lens 176 is a focusing lens that collimates the excitation light beam such that the focal point of the beam is in the center of the sample. The emission light (in this case, the light transmitted through the sample) is collected by the bottom absorbance read head 184. The transmitted light may then be directed to an absorbance-specific light detector (e.g., a photodiode, not shown in FIG. 1). This position may also be utilized for luminescence measurements in conjunction with an emission filter holder 160. As appreciated by persons skilled in the art, luminescence measurements do not utilize excitation light, but rather luminescence is initiated by adding an appropriate reagent to the sample. Luminescent emission light from the sample is collected by the top fluorescence/luminescence lens 180, and is directed through the emission optics 120 to the light detector 112.

Position 2: This position may be utilized for bottom-read fluorescence measurements in conjunction with the excitation monochromator 132 and an emission monochromator 164, or in conjunction with the excitation filter holder 136 and the emission monochromator 164. The excitation light is directed via an excitation optical fiber (not shown) to the bottom fluorescence read head 188, which focuses the excitation light beam on the sample (thereby irradiating the sample from the bottom of the multi-well plate). The emission light (in this case, the fluorescence light emitted from the sample) is collected by the bottom fluorescence read head 188. The emission light may then be directed to main optical path selection device 172 via an emission optical fiber (not shown), and then onward through the emission optics 120 to the light detector 112.

Position 3: This position may be utilized for bottom-read fluorescence measurements in conjunction with the excitation monochromator 132 and the emission filter holder 160, or in conjunction with the excitation filter holder 136 and the emission filter holder 160. The excitation optical fiber, bottom fluorescence read head 188, and emission optical fiber are utilized as just described.

Position 4: This position may be utilized for top-read fluorescence measurements in conjunction with the excitation monochromator 132 and the emission monochromator 164, or in conjunction with the excitation filter holder 136 and the emission monochromator 164. At this position, the emission light is directed to the top fluorescence/luminescence lens 180, which focuses the excitation light beam on the sample (thereby irradiating the sample from the top of the multi-well plate). The emission light may then be collected by the same top fluorescence/luminescence lens 180, and then onward through the emission optics 120 to the light detector 112. This position may also be utilized for luminescence measurements in conjunction with the emission monochromator 164. Luminescent emission light from the sample is collected by the top fluorescence/luminescence lens 180 and then directed through the emission optics 120 to the light detector 112.

Position 5: This position may be utilized for top-read fluorescence measurements in conjunction with the excitation filter holder 136 and the emission filter holder 160. The top fluorescence/luminescence lens 180 and the light detector 112 may be utilized in this case as described above. This position may also be utilized for fluorescence polarization measurements or time-resolved fluorescence measurements in conjunction with the excitation filter holder 136 and the emission filter holder 160.

As evident from comparing the various Positions 0-5 of the main optical path selection device 172 as implemented in the present embodiment, the position of the main optical path selection device 172 determines whether the emission light is transmitted through the emission monochromator 164 or through the emission filter holder 160. More generally, the various types of optics-based measurements made possible by the sample analyzing apparatus 100 may be carried out in conjunction with any combination of the excitation monochromator 132, excitation filter holder 136, emission monochromator 164, and emission filter holder 160.

In some embodiments, the sample analyzing apparatus 100 may further include a liquid dispensing system (e.g., injector needle(s), tubing, pump(s), reservoir(s), etc., not shown) configured for adding a liquid to the sample (e.g., into selected wells or onto selected blots of the sample support disposed on the sample carrier 104) before or after the sample has been operatively positioned in the sample analyzing apparatus 100. For example, a labeling agent may be added to the sample for fluorescence, luminescence or other types of measurements, as appreciated by persons skilled in the art. In some embodiments, two or more different types of reagents may be added.

The sample analyzing apparatus 100 may further include a system controller (e.g., a computing device) 190. As appreciated by persons skilled in the art, the system controller 190 may include one or more modules configured for controlling, monitoring and/or timing various functional aspects of the sample analyzing apparatus 100, and/or for receiving data or other signals from the sample analyzing apparatus 100 such as measurement signals from the light detector 112 and transmitting control signals to the light detector 112 and/or other components. For example, the system controller 190 may be configured for coordinating the operations (e.g., movements and positions) of the sample carrier 104, the cartridge module 124 (if provided), the excitation monochromator 132, the excitation filter holder 136, the excitation path selection device 148, the emission monochromator 156, the emission filter holder 160, and the main optical path selection device 172. For all such purposes, the system controller 190 may communicate with various components of the sample analyzing apparatus 100 via wired or wireless communication links. In typical embodiments, the system controller 190 includes a main electronic processor providing overall control, and may include one or more electronic processors configured for dedicated control operations or specific signal processing tasks. The system controller 190 may also include one or more memories and/or databases for storing data and/or software. The system controller 190 may also include a computer-readable medium that includes instructions for performing any of the methods disclosed herein. The functional modules of the system controller 190 may comprise circuitry or other types of hardware (or firmware), software, or both. For example, the modules may include signal processing (or data acquisition) circuitry for receiving measurement signals from the light detector 112 and software for processing the measurement signals such as for generating graphical data. The system controller 190 may also include or communicate with one or more types of user interface devices, such as user input devices (e.g., keypad, touch screen, mouse, and the like), user output devices (e.g., display screen, printer, visual indicators or alerts, audible indicators or alerts, and the like), a graphical user interface (GUI) controlled by software, and devices for loading media readable by the electronic processor (e.g., logic instructions embodied in software, data, and the like). The system controller 190 may include an operating system (e.g., Microsoft Windows® software) for controlling and managing various functions of the system controller 190.

According to some embodiments, an experiment entailing optical measurement utilizing the sample analyzing apparatus 100 may be implemented as follows. The sample or samples are introduced into the sample analyzing apparatus 100 and placed in a proper operating position relative to optics and other components of the sample analyzing apparatus 100. Generally, the "operating" position of the sample is an "optically aligned" position, i.e., a position that establishes an optical path sufficient for optical data acquisition from the sample. Depending on the experiment, the operating position may also correspond to the sample being "fluidly aligned" with the sample analyzing apparatus 100, i.e., positioned so as to be able to dispense fluid onto the sample such as by operating a liquid dispensing system as described above. Sample introduction may entail loading one or more samples in one or more wells of a microplate or other type of sample support (e.g., preparing samples in accordance with blotting techniques such as Western Blot, as appreciated by persons skilled in the art), and loading or mounting the sample support in the sample analyzing apparatus 100, such as with the use of the sample carrier 104 described above. Depending on the sample and the type of measurement to be made, the sample may be subjected to preparation or treatment (incubation, mixing, homogenization, centrifuging, buffering, reagent addition, analytical separation such as solid phase extraction, chromatography, electrophoresis, etc.) prior to being positioned in the sample analyzing apparatus 100, as appreciated by persons skilled in the art.

In addition to sample introduction, the sample analyzing apparatus 100 or certain components thereof (optics, electronics, etc.) may need to be configured for implementing the specific type of measurement to be made. For example, if cartridge-based, the appropriate cartridge (or cartridges) may be installed in the cartridge module 124 of the sample analyzing apparatus 100. After installing a cartridge, optics provided in the cartridge become part of the optical circuit within the apparatus housing 128 of the sample analyzing apparatus 100. For example, the cartridge optics may be aligned with (in optical communication with) the excitation optics 116, emission optics 120, and/or interface optics 126. Installing the cartridge results in establishing electrical paths for transmitting power, data and control signals to and/or from the cartridge.

The sample is then processed as necessary to induce the emission of photons from the sample for measurement. In the case of luminescence measurement, reagents may be added to induce a luminescent response, such as by operating a liquid dispensing system as described above. In the case of fluorescence measurement, the light source 108 and associated excitation optics 116 (and possibly a cartridge and/or the interface optics 126, as described above) are utilized to irradiate or excite the sample to induce a fluorescent response. Fluorescence measurement may additionally entail the addition of reagents to induce the fluorescent response. In the case of either luminescence or fluorescence measurement, the emission optics 120 (and possibly a cartridge and/or the interface optics 126, as described above) are utilized to collect the emission light from the sample and direct the emission light to the light detector 112. The light detector 112 converts these optical signals into electrical signals (detector signals, or measurement signals) and transmits the electrical signals to signal processing circuitry, such as may be provided by a system controller 190 of the sample analyzing apparatus 100 as described above.

In the case of absorbance measurement, the light source 108 and associated excitation optics 116 (and possibly a cartridge and/or the interface optics 126, as described above) are utilized to irradiate the sample. In this case, the "emission" light is the light transmitted through the sample, which is attenuated in comparison to the excitation light incident on the sample due to absorbance by the sample of some of the light. The transmitted ("emission") light may be directed to an absorbance detector that may be separate from the illustrated light detector 112, as described above.

For any of the optical measurement techniques implemented, multiple samples may be processed. For example, the sample support on or in which the multiple samples are provided may be moved (such as by using the sample carrier 104) to sequentially align each sample with the optics being utilized for the experiment, whereby measurements are taken from all samples sequentially.

An example of a method for analyzing a sample by optical-based measurement, involving selection of the excitation path, will now be described. Generally, this method may be implemented in conjunction with an optical-based measurement requiring excitation or irradiation of the sample by excitation light, examples of which include fluorescence-based and absorbance-based measurements. Depending on the specific method to be performed, it may be desirable to restrict the excitation light utilized to excite or irradiate the sample to a specific wavelength (or narrow band of wavelengths). Thus, the method may entail selecting the wavelength of the excitation light to be transmitted to the sample. Additionally, the method may entail selecting the modality by which the wavelength is to be selected (i.e., the wavelength to which the excitation light is to be restricted). In one embodiment, selection of the wavelength-selecting modality entails selecting whether to employ the excitation monochromator 132 as a first stage of wavelength selection and the excitation filter holder 136 as a second stage of wavelength selection, or to employ the excitation filter holder 136 as the sole modality for wavelength selection. Thus, the method may include selecting between the first excitation light path 140 and the second excitation light path 144. As described above, the first excitation light path 140 directs excitation light from the light source 108, through the excitation monochromator 132 (i.e., to the excitation monochromator 132 and then onward to the excitation filter holder 136), through the excitation filter holder 136, and to the sample. On the other hand, the second excitation light path 144 directs excitation light from the light source 108, through the excitation filter holder 136, and to the sample while bypassing the excitation monochromator 132. Depending on whether the first excitation light path 140 or the second excitation light path 144 has been selected, either the excitation filter holder 136, or both the excitation filter holder 136 and the excitation monochromator 132, is set (adjusting by moving) so as to select the desired wavelength for further transmission toward the sample.

The excitation filter holder 136 is set by selecting, from among the plurality of excitation filters mounted to the excitation filter holder 136, the excitation filter that has the optical transmission characteristics effective for passing the desired wavelength while blocking other wavelengths of the excitation light. The excitation filter holder 136 is then moved (by sliding or rotation) so as to insert the selected excitation filter into the selected one of the first excitation light path 140 and the second excitation light path 144. The excitation monochromator 132 is set by moving (typically rotating) the excitation monochromator 132 to a position at which the excitation monochromator 132 will transmit the excitation light at the selected wavelength along the first excitation light path 140. In a typical embodiment, the excitation monochromator 132 receives the broadband excitation light from the light source 108 and disperses the excitation light into different wavelengths, which propagate away from the excitation monochromator 132 as individual beams in different directions (angles) relative to each other. The position of the excitation monochromator 132 dictates which of the wavelength-specific beams is aligned with an exit slit and thus is able to be transmitted onward to the excitation filter holder 136, while the non-selected wavelengths are blocked and do not pass through the exit slit. Changing the position of the excitation monochromator 132 thus changes which wavelength is transmitted onward.

After selecting the excitation wavelength and the excitation light path (the first excitation light path 140 or the second excitation light path 144), the excitation light generated at the light source 108 is transmitted along selected excitation light path 140 or 144. The resulting wavelength-selected excitation light is then transmitted to the sample. The method may then proceed as generally described elsewhere herein. Thus, in response to being irradiated by the excitation light, the sample produces emission light (which may be light transmitted through the sample in the case of measuring absorbance, and the emission light is transmitted to and measured by the light detector 112 (or an absorbance-specific light detector).

Depending on the embodiment, the method may include operation and/or use of other components of the sample analyzing apparatus 100, such as one or more cartridges of the cartridge module 124, the interface optics 126, the main optical path selection device 172, the emission monochromator 164, the emission filter holder 160, etc., all as described elsewhere herein.

Figure 3:
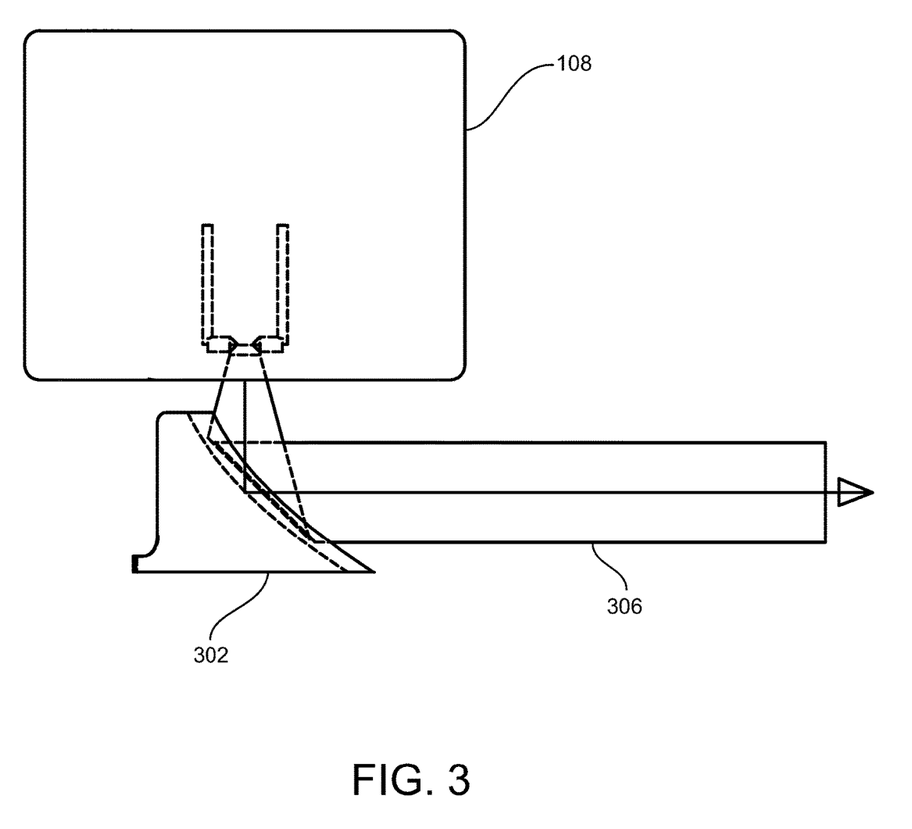
FIG. 3 is a schematic elevation view of an example of a light source and a component of an excitation path selection device that is configured to select (switch) between a first excitation light path and a second excitation light path, according to an embodiment disclosed herein.

FIG. 3 is a schematic elevation view of an example of the light source 108 and a component of the excitation path selection device 148 that is configured to select (switch)

between the first excitation light path 140 and the second excitation light path 144. Generally, the excitation path selection device 148 may include one or more components such as beam-steering devices that are movable to effect the selection of the excitation light path. In the embodiment illustrated in FIG. 3, the excitation path selection device 148 includes a beam-steering device in the form of a parabolic mirror 302. In FIG. 3, the excitation path selection device 148 has been moved to a position at which the parabolic mirror 302 is in optical alignment with the light source 108 and the excitation filter holder 136. At this position, the parabolic mirror 302 is oriented so as to reflect an excitation light beam 306 in the direction of the second excitation light path 144, thus transmitting the excitation light beam 306 directly to the excitation filter holder 136 while bypassing the excitation monochromator 132.

Figure 4:
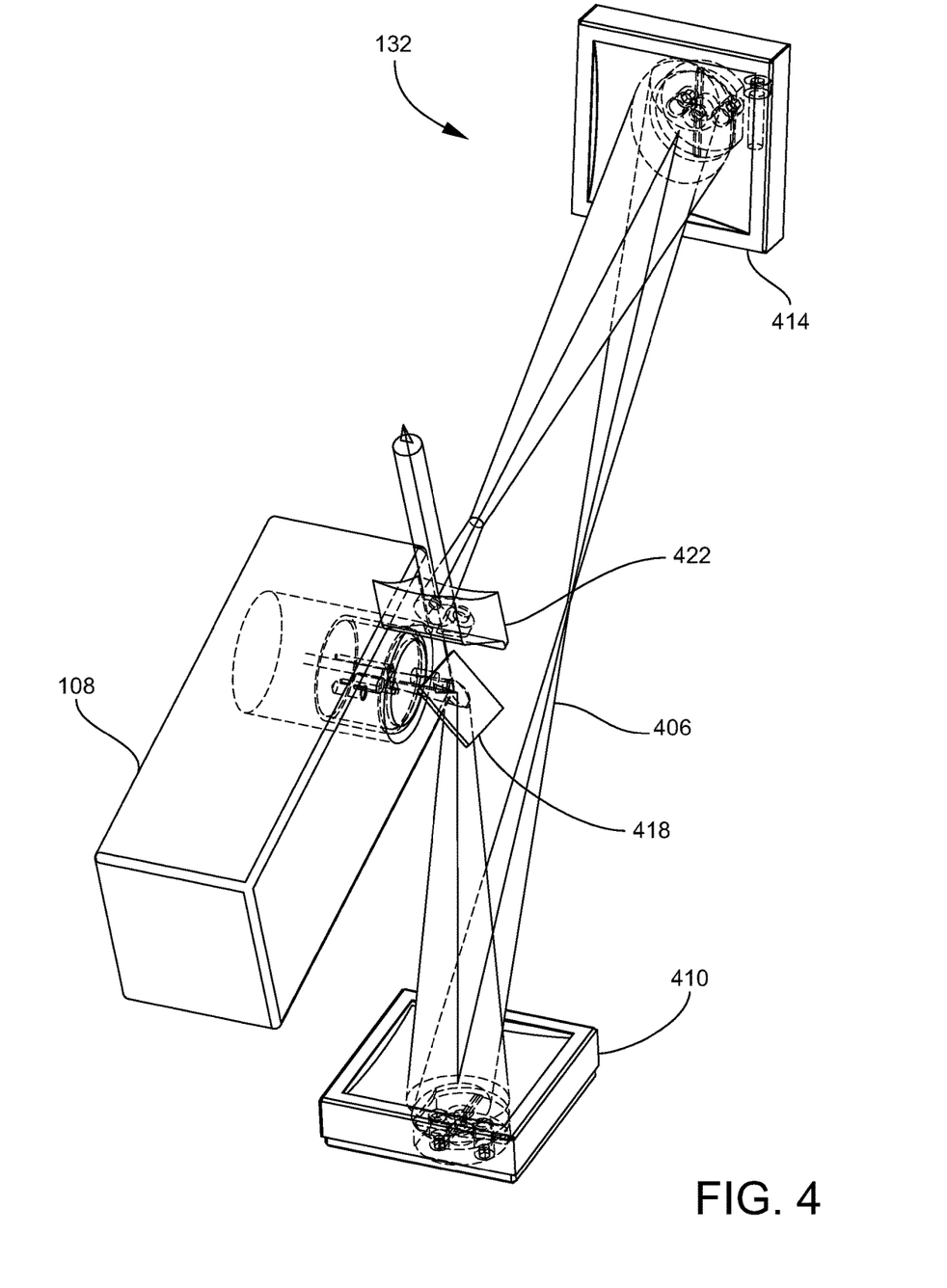
FIG. 4 is a schematic perspective view of an example of a light source, an excitation monochromator, and other components of the excitation path selection device, according to an embodiment disclosed herein.

FIG. 4 is a schematic perspective view of an example of the light source 108, the excitation monochromator 132, and other components of the excitation path selection device 148. In the embodiment illustrated in FIG. 4, the excitation monochromator 132 is configured as a double monochromator. As appreciated by persons skilled in the art, a double monochromator includes two diffraction gratings positioned in series to improve the elimination of stray light from the light beam being processed. As shown in FIG. 4, the excitation monochromator 132 includes a first diffraction grating 410 and a second diffraction grating 414 arranged in series. The first diffraction grating 410 and the second diffraction grating 414 are rotatable so as to select a specific wavelength of excitation light generated by the light source 108. Also in the embodiment illustrated in FIG. 4, the excitation path selection device 148 includes two additional beam-steering devices in the form of a flat mirror 418 and a parabolic mirror 422. In FIG. 4, the excitation path selection device 148 has been moved to a position at which the flat mirror 418 is in optical alignment with the light source 108 and the first diffraction grating 410, and the parabolic mirror 422 is in optical alignment with the second diffraction grating 414 and the excitation filter holder 136. At this position, the flat mirror 418 is oriented so as to reflect an excitation light beam 406 toward the first diffraction grating 410, which transmits the excitation light beam 406 to the second diffraction grating 414. Also at this position, the parabolic mirror 422 is oriented so as to receive the wavelength-specific component of the excitation light beam 406 from the second diffraction grating 414 and reflect the wavelength-specific component as a beam toward the excitation filter holder 136. Hence, FIG. 4 (at least partially) illustrates an example of the first excitation light path 140.

Figure 5:
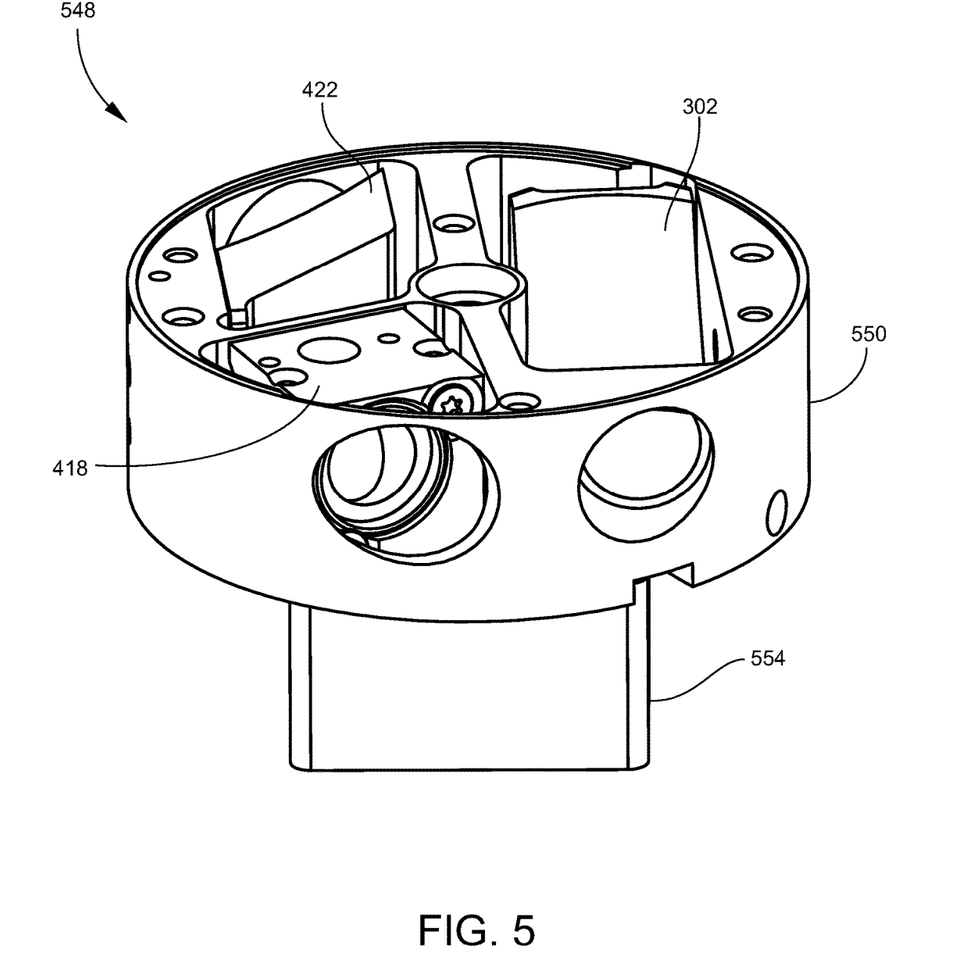
FIG. 5 is a schematic perspective view of an example of an excitation path selection device according to an embodiment disclosed herein.

FIG. 5 is a schematic perspective view of an example of an excitation path selection device 548 according to an embodiment. The excitation path selection device 548 may correspond to the excitation path selection device 148 described above and illustrated in FIG. 1. In the illustrated embodiment, the excitation path selection device 548 includes a movable base 550 on which all of the beam-steering devices utilized to select (switch) between the first excitation light path 140 and the second excitation light path 144 (e.g., the parabolic mirror 302, the flat mirror 418, and the parabolic mirror 422) may be mounted. The base 550 is movable (e.g., by rotation) between a first position in which the first excitation light path 140 is active (with the flat mirror 418 and parabolic mirror 422 positioned as shown in FIG. 4), and a second position in which the second excitation light path 144 is active (with the parabolic mirror 302 positioned as shown in FIG. 3). Stated in another way, the base is movable between a first position at which the parabolic mirror 302 is aligned with the light source 108, and a second position at which the flat mirror 418 is aligned with the light source 108. Movement of the base 550 may be automated by appropriately coupling the base 550 to a motor 554, as appreciated by persons skilled in the art. As the parabolic mirror 302, the flat mirror 418, and the parabolic mirror 422 move together with the base, switching between the first excitation light path 140 and the second excitation light path 144 requires movement of only a single component, namely the base 550.

Figure 6:
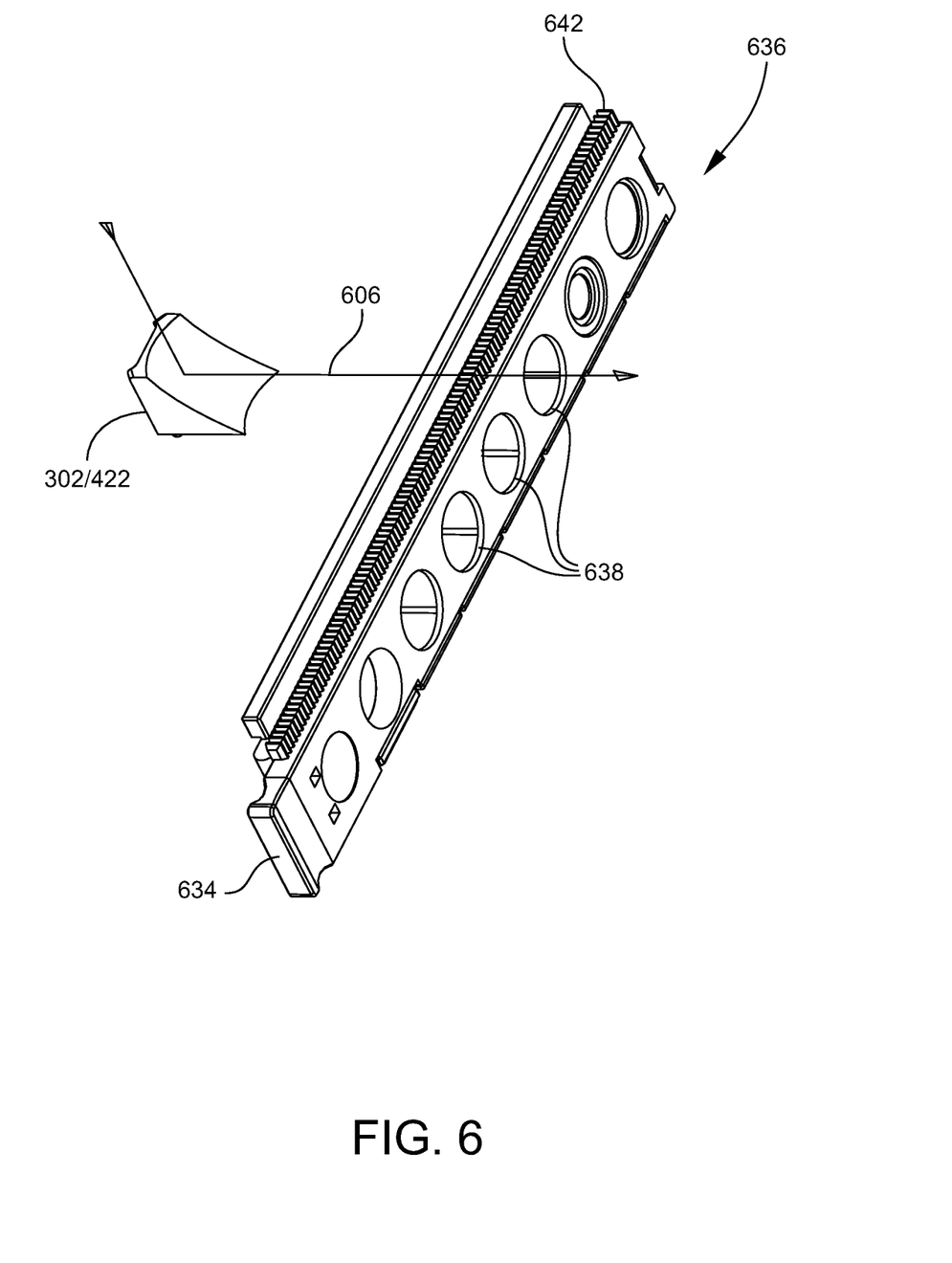
FIG. 6 is a schematic perspective view of an example of an excitation filter holder and a component of the excitation path selection device, according to an embodiment disclosed herein.

FIG. 6 is a schematic perspective view of an example of an excitation filter holder 636 according to an embodiment, and a component of the excitation path selection device 148 or 548. The excitation filter holder 636 may correspond to the excitation filter holder 136 described above and illustrated in FIG. 1. For example, when the first excitation light path 140 is selected the component may be the parabolic mirror 422 described above and illustrated in FIG. 4, or when the second excitation light path 144 is selected the component may be the parabolic mirror 302 described above and illustrated in FIG. 3. In the embodiment illustrated in FIG. 6, the excitation filter holder 636 includes a structural body 634 and a plurality of receptacles at which respective excitation filters 638 are mounted. In the present example, the excitation filter holder 636 is linearly movable (i.e., slidable) so as to insert a selected excitation filter 638 into the path of an excitation light beam 606 traveling in either the first excitation light path 140 or the second excitation light path 144. Also in the present example, the excitation filter holder 636 includes a rack 642 to effect linear movement. A rotating pinion or other suitable component (driven by a suitable motor and intervening transmission components) may engage the rack 642 to drive the linear movement of the excitation filter holder 636, which may be supported on appropriate bearings or linear guide, as appreciated by persons skilled in the art.

It will be understood that one or more of the processes, sub-processes, and process steps described herein may be performed by hardware, firmware, software, or a combination of two or more of the foregoing, on one or more electronic or digitally-controlled devices. The software may reside in a software memory (not shown) in a suitable electronic processing component or system such as, for example, the system controller (computing device) 190 schematically depicted in FIG. 2. The software memory may include an ordered listing of executable instructions for implementing logical functions (that is, "logic" that may be implemented in digital form such as digital circuitry or source code, or in analog form such as an analog source such as an analog electrical, sound, or video signal). The instructions may be executed within a processing module, which includes, for example, one or more microprocessors, general purpose processors, combinations of processors, digital signal processors (DSPs), application specific integrated circuits (ASICs), or field-programmable gate arrays (FPGAs). Further, the schematic diagrams describe a logical division of functions having physical (hardware and/or software) implementations that are not limited by architecture or the physical layout of the functions. The examples of systems described herein may be implemented in a variety of configurations and operate as hardware/software components in a single hardware/software unit, or in separate hardware/software units.

The executable instructions may be implemented as a computer program product having instructions stored therein which, when executed by a processing module of an electronic system (e.g., the system controller 190 shown in FIG. 2), direct the electronic system to carry out the instructions. The computer program product may be selectively embodied in any non-transitory computer-readable storage medium for use by or in connection with an instruction execution system, apparatus, or device, such as an electronic computer-based system, processor-containing system, or other system that may selectively fetch the instructions from the instruction execution system, apparatus, or device and execute the instructions. In the context of this disclosure, a computer-readable storage medium is any non-transitory means that may store the program for use by or in connection with the instruction execution system, apparatus, or device. The non-transitory computer-readable storage medium may selectively be, for example, an electronic, magnetic, optical, electromagnetic, infrared, or semiconductor system, apparatus, or device. A non-exhaustive list of more specific examples of non-transitory computer readable media include: an electrical connection having one or more wires (electronic); a portable computer diskette (magnetic); a random access memory (electronic); a read-only memory (electronic); an erasable programmable read only memory such as, for example, flash memory (electronic); a compact disc memory such as, for example, CD-ROM, CD-R, CD-RW (optical); and digital versatile disc memory, i.e., DVD (optical). Note that the non-transitory computer-readable storage medium may even be paper or another suitable medium upon which the program is printed, as the program can be electronically captured via, for instance, optical scanning of the paper or other medium, then compiled, interpreted, or otherwise processed in a suitable manner if necessary, and then stored in a computer memory or machine memory.

It will also be understood that the term "in signal communication" as used herein means that two or more systems, devices, components, modules, or sub-modules are capable of communicating with each other via signals that travel over some type of signal path. The signals may be communication, power, data, or energy signals, which may communicate information, power, or energy from a first system, device, component, module, or sub-module to a second system, device, component, module, or sub-module along a signal path between the first and second system, device, component, module, or sub-module. The signal paths may include physical, electrical, magnetic, electromagnetic, electrochemical, optical, wired, or wireless connections. The signal paths may also include additional systems, devices, components, modules, or sub-modules between the first and second system, device, component, module, or sub-module.

More generally, terms such as "communicate" and "in . . . communication with" (for example, a first component "communicates with" or "is in communication with" a second component) are used herein to indicate a structural, functional, mechanical, electrical, signal, optical, magnetic, electromagnetic, ionic or fluidic relationship between two or more components or elements. As such, the fact that one component is said to communicate with a second component is not intended to exclude the possibility that additional components may be present between, and/or operatively associated or engaged with, the first and second components.

It will be understood that various aspects or details of the invention may be changed without departing from the scope of the invention. Furthermore, the foregoing description is for the purpose of illustration only, and not for the purpose of limitation—the invention being defined by the claims.

What is claimed is:

1. A method for analyzing a sample by an optical-based measurement, the method comprising:
   selecting between a first excitation light path and a second excitation light path, wherein:
      the first excitation light path directs excitation light from a light source, through an excitation monochromator, through an excitation filter, and to the sample; and
      the second excitation light path directs excitation light from the light source, through the excitation filter, and to the sample while bypassing the excitation monochromator;
   generating excitation light at the light source;
   irradiating the sample by transmitting the generated excitation light along the selected one of the first excitation light path and the second excitation light path, wherein irradiating the sample produces emission light; and
   measuring the emission light by transmitting the emission light to a light detector.

2. The method of claim 1, comprising, after selecting, operating an excitation light path selection device to direct the excitation light along the selected one of the first excitation light path and the second excitation light path.

3. The method of claim 2, wherein the excitation light path selection device comprises an optical beam steering device configured to receive the excitation light from the light source, and operating the excitation light path selection device comprises moving the optical beam steering device.

4. The method of claim 2, wherein:
   the excitation light path selection device comprises a movable base, a first optical beam steering device mounted to the base, and a second optical beam steering device mounted to the base;
   operating the excitation light path selection device comprises moving the base to a first position or a second position;
   at the first position, the first optical beam steering device is positioned to receive the excitation light and direct the excitation light to the first excitation light path; and
   at the second position, the second optical beam steering device is positioned to receive the excitation light and direct the excitation light to the second excitation light path.

5. The method of claim 1, comprising selecting a wavelength at which the excitation light is to be transmitted to the sample.

6. The method of claim 5, wherein selecting the wavelength comprises selecting the excitation filter from a plurality of different excitation filters having different wavelength transmission characteristics, and wherein the selected excitation filter is configured to transmit the excitation light at the selected wavelength.

7. The method of claim 6, wherein the plurality of different excitation filters are mounted to an excitation filter holder, and selecting the excitation filter comprises moving the excitation filter holder to insert the selected excitation filter into the selected one of the first excitation light path and the second excitation light path.

8. The method of claim 6, wherein the first excitation light path is selected, and selecting the wavelength further comprises moving the excitation monochromator to a position at which the excitation monochromator transmits the excitation light at the selected wavelength along the first excitation light path.

9. The method of claim 1, wherein measuring the emission light comprises measuring absorbance or fluorescence.

10. The method of claim 1, comprising selecting between a first emission light path and a second emission light path, wherein:

the first emission light path directs the emission light through an emission monochromator, through an emission filter, and to the light detector;

the second emission light path directs the emission light through the emission filter and to the light detector while bypassing the emission monochromator; and transmitting the emission light to the light detector comprises transmitting the emission light along the selected one of the first emission light path and the second emission light path.

11. The method of claim 1, comprising selecting an emission wavelength at which the emission light is to be transmitted to the light detector.

12. The method of claim 11, wherein selecting the emission wavelength comprises selecting an emission filter from a plurality of different emission filters having different wavelength transmission characteristics, and wherein the selected emission filter is configured to transmit the emission light at the selected wavelength.

13. The method of claim 12, wherein the plurality of different emission filters are mounted to an emission filter holder, and selecting the emission filter comprises moving the emission filter holder to insert the selected emission filter into the selected one of the first emission light path and the second emission light path.

14. The method of claim 12 wherein the first emission light path is selected, and selecting the emission wavelength further comprises moving the emission monochromator to a position at which the emission monochromator transmits the emission light at the selected emission wavelength along the first emission light path.

15. A sample analyzing apparatus for performing an optical-based measurement on a sample, the sample analyzing apparatus comprising:
a light source configured for generating excitation light;
a light detector configured for measuring the emission light; and
an excitation light path selection device configured for selecting between the first excitation light path and the second excitation light path in accordance with the method of claim 1.

16. The sample analyzing apparatus of claim 15, wherein the excitation light path selection device comprises an optical beam steering device configured to receive the excitation light from the light source, and being movable to direct the excitation light along the selected one of the first excitation light path and the second excitation light path.

17. A sample analyzing apparatus for performing an optical-based measurement on a sample, the sample analyzing apparatus comprising:
a light source configured for generating excitation light;
excitation optics configured for directing the excitation light from the light source to the sample, wherein the sample produces emission light in response to being irradiated by the excitation light;
a light detector configured for measuring the emission light; and
emission optics configured for directing the emission light from the sample to the light detector, wherein:
the excitation optics comprise an excitation filter, an excitation monochromator, and an excitation light path selection device configured for selecting between a first excitation light path and a second excitation light path;
the first excitation light path directs excitation light from a light source, through an excitation monochromator, through an excitation filter, and to the sample; and
the second excitation light path directs excitation light from the light source, through the excitation filter, and to the sample while bypassing the excitation monochromator.

18. The sample analyzing apparatus of claim 17, wherein the excitation light path selection device comprises an optical beam steering device configured to receive the excitation light from the light source, and being movable to direct the excitation light along the selected one of the first excitation light path and the second excitation light path.

19. The sample analyzing apparatus of claim 17, wherein:
the excitation light path selection device comprises a movable base, a first optical beam steering device mounted to the base, and a second optical beam steering device mounted to the base;
the movable base is configured for moving between a first position and a second position;
at the first position, the first optical beam steering device is positioned to receive the excitation light and direct the excitation light to the first excitation light path; and
at the second position, the second optical beam steering device is positioned to receive the excitation light and direct the excitation light to the second excitation light path.

20. The sample analyzing apparatus of claim 17, comprising an excitation filter holder, and a plurality of different excitation filters mounted to the excitation filter holder and having different wavelength transmission characteristics, wherein the excitation filter holder is movable to insert a selected one of the excitation filters into the selected one of the first excitation light path and the second excitation light path.

* * * * *